United States Patent
Bajgrowicz

(10) Patent No.: US 8,030,524 B2
(45) Date of Patent: Oct. 4, 2011

(54) ORGANIC COMPOUNDS

(75) Inventor: Jerzy A. Bajgrowicz, Zurich (CH)

(73) Assignee: Gibaudan SA, Vernier (CH)

( * ) Notice: Subject to any disclaimer, the term of this patent is extended or adjusted under 35 U.S.C. 154(b) by 262 days.

(21) Appl. No.: 12/513,263

(22) PCT Filed: Nov. 2, 2007

(86) PCT No.: PCT/CH2007/000545
§ 371 (c)(1),
(2), (4) Date: May 1, 2009

(87) PCT Pub. No.: WO2008/052379
PCT Pub. Date: May 8, 2008

(65) Prior Publication Data
US 2010/0069508 A1    Mar. 18, 2010

(30) Foreign Application Priority Data
Nov. 3, 2006 (GB) .................................. 0621805.1

(51) Int. Cl.
*C07C 49/105* (2006.01)

(52) U.S. Cl. .......................... 568/374; 568/445; 512/18

(58) Field of Classification Search .................. 568/374, 568/445; 512/18
See application file for complete search history.

(56) References Cited

U.S. PATENT DOCUMENTS
5,929,291 A    7/1999  Bajgrowicz

FOREIGN PATENT DOCUMENTS
EP    0466019 A2    1/1992
EP    0801049 A2    10/1997
WO    2006102777 A1    10/2006

OTHER PUBLICATIONS

Journal of Chemical Information and Computer Sciences vol. 43, No. 1, 2003, pp. 259-266, Assia Kovatcheva et al., "QSAR modeling of x-campholenic derivatives with sandalwood odor".

Bajgrowicz J A et al.: "Synthesis and Structure Elucidation of a New Potent Sandalwood-Oil Substitute" Helvetica Chimica Acta, Verlad Helvetica CHemica Acta. Basel, CH vol. 81, 1998, pp. 1349-1358, XP002362562.

Fragrance Chemistry, The Science of the Sense of Smell, edited by Ernst T. Theimer, 1982, Academic Press, pp. 426-429.

*Primary Examiner* — Yong Chong
(74) *Attorney, Agent, or Firm* — Norris McLaughlin & Marcus, P.A.

(57) ABSTRACT

Described are 2,2,3-trimethylcyclopentane derivatives of formula 1

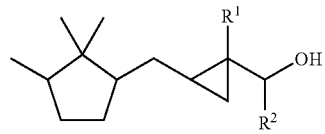

wherein $R^1$ is methyl or ethyl; and $R^2$ is hydrogen, methyl or ethyl.

The invention furthermore relates to a method of their production a to fragrance compositions comprising them.

12 Claims, No Drawings

ORGANIC COMPOUNDS

This is an application filed under 35 USC 371 of PCT/CH2007/000545.

The present invention refers to a novel class of 2,2,3-trimethylcyclopentane derivatives possessing an exceptional natural sandalwood oil odour profile. In addition the present invention refers to fragrance compositions comprising such derivatives.

Sandalwood oils, in particular East India sandalwood oil, are among the most appreciated but unfortunately also most scarce perfumery raw materials. As a result, effective synthetic substitutes that will give the same natural odour, particularly for use in fine fragrances, have been sought for more than 50 years.

Compounds based on a saturated ring system, such as 3-methyl-5-(2,2,3-trimethylcyclopentyl)pent-3-en-2-ol (A), are described, for example, in EP 0 466 019. According to the description, the odour notes are characterised as being fruity, flowery, with woody (in particular) side notes. According to Ernst-Joachim Brunke et al. (in "Fragrance Chemistry, the Science of the Sense of Smell"; Theimer E. T.; Ed., Academic Press, New York, 1982, pages 424-429) saturation of the double bond in the cyclopentene system of 2-methyl-4-(2,2,3-trimethylcyclopent-3-enyl)butan-1-ol (compound B wherein R=H) results in a weak dry-woody smell.

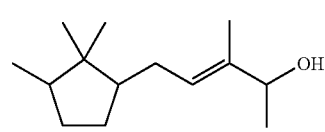

A

Brunke also observed that the loss of sandalwood odor is detectable after hydrogenation of 3-methyl-5-(2,2,3-trimethylcyclopent-3-enyl)pentan-2-ol (compound B wherein R is methyl) and of 4-methyl-6-(2,2,3-trimethylcyclopent-3-enyl)hexan-3-ol (compound B wherein R is ethyl).

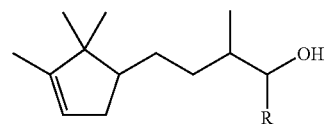

B

Brunke finally stated that to get the fragrance of sandalwood a double bond at C-3 in the ring is necessary, which however can be replaced by a cyclopropane ring, an ether group or an environment with steric hindrance. With other words, the loss of the structural feature that enhances the electronic density in the cyclopropane ring system, which can be either a carbon-carbon double bond or an isoelectronic cyclopropane ring is therefore most likely to bring about a loss or reduction of their typical sandalwood odour notes.

Surprisingly, we have now found that certain 2,2,3-trimethylcyclopentane derivatives, i.e. compounds based on a saturated cyclopentane system, possess an exceptionally natural sandalwood oil odour.

Accordingly, the present invention refers in one of its aspects to compounds of formula 1

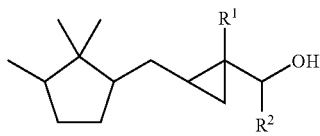

1 wherein
$R^1$ is methyl or ethyl; and
$R^2$ is hydrogen, methyl or ethyl.

The compounds of formula 1 may comprise several chiral centres and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or by departing from chiral starting materials, e.g. starting from enantiomerically pure or enriched raw materials such as terpenoids, and/or by applying stereoselective synthesis.

Thus, the present invention refers in a further aspect to compounds of formula 1 enriched in either a compound of formula 1R or 1S, preferably in the ratio from about 1:9 to about 9:1 (R/S), e.g. from about 2:3, or about 2:7 to about 6:1, or about 11:1, or pure enantiomers of compounds of formula 1, namely compounds of formula 1R or 1S

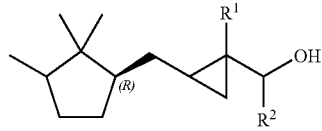

1R

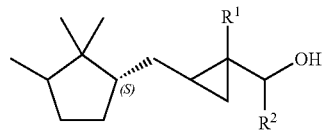

1S wherein $R^1$ and $R^2$ have the same meaning as given for formula 1 above.

Particularly preferred compounds of formula 1 are [1-ethyl-2-[(2,2,3-trimethylcyclopentyl)methyl]cyclopropyl]methanol, [1-methyl-2-[(2,2,3-trimethylcyclopentyl)methyl]cyclopropyl]methanol and 1-[1-methyl-2-[(2,2,3-trimethylcyclopentyl)methyl]cyclopropyl]ethanol.

The compounds according to the present invention may be used alone or in combination with known odorant molecules selected from the extensive range of natural and synthetic molecules currently available, such as essential oils and extracts, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

The following list comprises examples of known odorant molecules, which may be combined with the compounds of the present invention:
  essential oils and extracts, e.g. tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol® (3-methyl-5-(2,2,3-trimethyl-3-cyclopenten-1-yl)-4-penten-2-ol), eugenol, farnesol, geraniol, Super Muguet™ (6-ethyl-3-methyl-6-octen-1-ol), linalool, menthol, nerol, phenylethyl alcohol, rhodinol, Sandalore® (5-(2,2,3-trimethyl-3-cyclopentenyl)-3-methylpentan-2-ol), terpineol or Timberol® (1-(2,2,6-trimethylcyclohexyl)hexan-3-ol);

aldehydes and ketones, e.g. anisaldehyde, α-amylcinnamaldehyde, Georgywood™ (1-(1,2,8,8-tetramethyl-1,2,3,4,5,6,7,8-octahydronaphthalen-2-yl)ethanone), hydroxycitronellal, Iso E Super® (1-(2,3,8,8-tetramethyl-1,2,3,4,5,6,7,8-octahydronaphthalen-2-yl)ethanone), Isoraldeine® (4-(2,6,6-trimethyl-2-cyclohexenyl)-3-methyl-3-buten-2-one), Hedione® (methyl (3-oxo-2-pentylcyclopentyl)acetate), Lilial® (3-(4-tert-butylphenyl)-2-methylpropanal), maltol, methyl cedryl ketone, methylionone, verbenone or vanillin;

ethers and acetals, e.g. Ambrox® (3a,6,6,9a-tetramethyldodecahydronaphtho[2,1-b]furan), geranyl methyl ether, rose oxide or Spirambrene (2,2,3',7',7'-pentamethylspiro(1,3-dioxan-5,2'-norcarane));

esters and lactones, e.g. benzyl acetate, cedryl acetate, γ-decalactone, Helvetolide® (2-[1-(3,3-dimethylcyclohexyl)ethoxy]-2-methylpropan-1-ol propanoate), γ-undecalactone or vetivenyl acetate;

macrocycles, e.g. ambrettolide, ethylene brassylate or Exaltolide® (oxacyclohexadecan-2-one);

heterocycles, e.g. isobutylquinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odorant ingredients. The proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in an alcoholic solution in amounts of from 0.1 to 30 weight percent, more preferably between 5 and 20 weight percent. However, these values are given only by way of example, since the experienced perfumer may also achieve effects or may create novel accords with lower or higher concentrations, e.g., up to about 50 weight percent based on the fragrance composition.

The compounds of the present invention may be employed into the fragrance application simply by directly mixing the fragrance composition with the fragrance application, or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application and consumer products resulting therefrom. The method comprises the incorporation therein of a compound of formula 1 as a fragrance ingredient, either by directly admixing the compound to the application or by admixing a fragrance composition comprising a compound of formula 1, which may then be mixed to a fragrance application, using conventional techniques and methods. Through the addition of an olfactorily acceptable amount of a compound of the present invention, the odor notes of a fragrance application will be improved, enhanced or modified.

Thus, the invention furthermore provides a method for improving, enhancing or modifying a fragrance application through the addition thereto of an olfactory acceptable amount of a compound of formula 1, or a mixture thereof.

The invention also provides a fragrance application comprising:

a) as odorant a compound of formula 1 or a mixture thereof; and b) a consumer product base.

As used herein, "fragrance application" means any products, such as fine fragrances, e.g. eaux de perfume and eaux de toilette; household products, e.g. detergents for dishwasher, surface cleaner, air freshener; laundry products, e.g. softener, bleach, detergent; body care products, e.g. after-shave lotion, shampoo, shower gel, shower and bath salt, hygiene product; and cosmetics, e.g. deodorants, vanishing creams, comprising an odorant. This list of products is given by way of illustration and is not to be regarded as being in any way limiting.

As used herein, "fragrance composition" means any composition comprising at least one odorant molecule and a diluent conventionally used in conjunction with odorants in fragrance compositions, such as dipropylenglycol (DPG), isopropylmyristate (IMP), triethylcitrate (TEC) and alcohol (e.g. ethanol).

The compounds of the present invention may be prepared according to Scheme 1, starting from α-campholenic aldehyde of any enantiomer ratio (pure (R) or (S) or any mixture of both enantiomers) via the corresponding dihydroanalogue (2,2,3-trimethylcyclopentylacetaldehyde; 2), as described for example in EP 0 466 019. The latter may be condensed with an aldehyde or ketone to give the α,β-unsaturated aldehyde or ketone 3. Reduction of 3 to the corresponding alcohols 4, followed by a cyclopropanation (e.g. using the Simmons-Smith reaction or the Yamamoto method) affords [2-[(2,2,3-trimethylcyclopentyl)methyl]cyclopropyl]methanols 1 as mixtures of stereoisomers. They may be separated or enriched in one or several stereoisomers by methodologies known in the art.

Scheme 1:

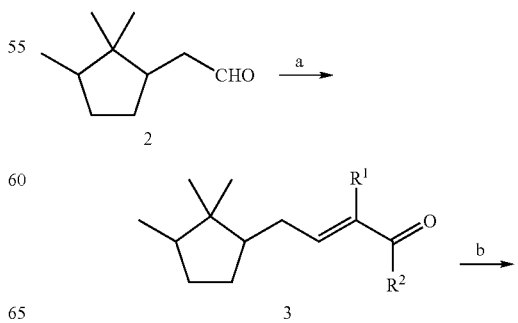

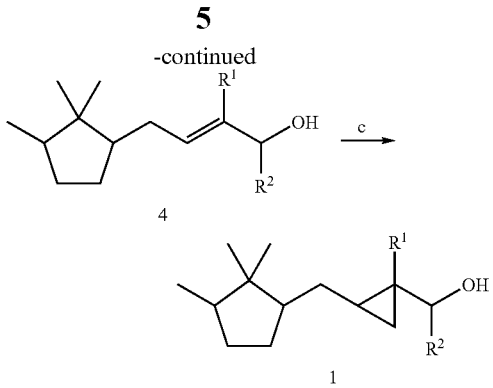

a) $R^1CH_2C(O)R^2$, base e.g. MeONa; b) $NaBH_4$ or $LiAlH_4$; c) $CH_2Br_2$, Zn, CuBr; or $CH_2I_2$, $Et_3Al$. $R^1$ and $R^2$ have the same meaning as given for formula 1 hereinabove.

The invention is now further described with reference to the following non-limiting examples. These examples are for the purpose of illustration only and it is understood that variations and modifications can be made by one skilled in the art.

All products described in the Examples were obtained starting from commercially available qualities of α-campholenic aldehyde of approximately 9:1 or 2:3 (R/S) enantiomer ratios. They were transformed into the corresponding enantiomeric mixtures of known dihydro-α-campholenic aldehyde (2). Flash chromatography: Merck silica gel 60 (230-400 mesh).

The reported NMR spectra were measured in $CDCl_3$; chemical shifts (δ) are reported in ppm downfield from TMS; coupling constants J in Hz.

EXAMPLE 1

[1-Ethyl-2-[[(1R)-2,2,3-trimethylcyclopentyl]methyl]cyclopropyl]methanol (1a); e. e. (enantiomeric excess)=80% a) 2-Ethyl-4-[(1R)-2,2,3-trimethylcyclopentyl]but-2-enal (3a)

Sodium methylate (0.75 g, 14 mmol) and butanal (21.6 g, 0.30 mol; dropwise during 2 h) were successively added to a stirred solution of (1R)-2,2,3-trimethylcyclopentylacetaldehyde (2, e. e.=80%; 25.0 g, 0.16 mol) in methanol (100 ml) at 5-10° C. After additional 18 h stirring at room temperature, acetic acid (3 ml) was added and the reaction mixture was extracted with MTBE (200 ml). The extract was washed with ice-cold brine (5×150 ml), dried ($MgSO_4$), concentrated in vacuo and the residue was distilled under reduced pressure to yield unreacted 2 (14 g) and 2-ethyl-4-[(1R)-2,2,3-trimethylcyclopentyl]but-2-enal (3a; 95° C./0.08 mbar) which was further purified by flash chromatography (MTBE/hexane 1:15; 8.7 g, 29% yield, colourless liquid; GC/MS: 2 isomeric pairs of enantiomers 3.5+91%).

Main isomer: $^1$H NMR: δ 9.35 (s, 1H), 6.45 (t, J=7.6, 1H), 2.46 (ddd, J=14.4, 7.4, 3.9, 1H), 2.27 (q, J=7.6, 2H), 2.12 (ddd, J=14.7, 10.6, 7.6, 1H), 1.87-1.72 (m, 2H), 1.60-1.48 (m, 2H), 1.26-1.19 (m, 2H), 0.98 (t, J=7.6, 3H), 0.93 (s, 3H), 0.86 (d, J=6.8, 3H), 0.59 (s, 3H). $^{13}$C NMR: δ 195.1 (d), 154.9 (d), 145.0 (s), 50.5 (d), 44.9 (d), 42.6 (s), 30.0 (t), 29.9 (t), 28.2 (t), 25.6 (q), 17.3 (t), 14.5 (q), 13.9 (q), 13.2 (q). MS: 208($M^+$, 1), 193(2), 165(3), 123(27), 111(23), 110(19), 109(88), 98(51), 95(42), 81(16), 69(100), 67(20), 55(10), 41(49).

b) 2-Ethyl-4-[(1R)-2,2,3-trimethylcyclopentyl]but-2-en-1-ol (4a)

2-Ethyl-4-[(1R)-2,2,3-trimethylcyclopentyl]but-2-enal (3a; 8.5 g, 41 mmol) was added dropwise within 10 min. to a stirred suspension of sodium borohydride (1.9 g, 50 mmol) in ethanol (100 ml) at 5-10° C. After additional 2 h stirring at room temperature, the reaction mixture was poured into an ice-cold 0.1 N HCl solution and extracted with MTBE (200 ml). The extract was washed with ice-cold brine (2×100 ml), dried ($MgSO_4$), concentrated in vacuo and the residue was distilled under reduced pressure to give 2-ethyl-4-[(1R)-2,2,3-trimethylcyclopentyl]but-2-en-1-ol (4a) which was further purified by flash chromatography (MTBE/hexane 1:5; 5.8 g, 68% yield, colourless liquid; GC/MS: 2 isomeric pairs of enantiomers 0.5+88.5%).

Main isomer: $^1$H NMR: δ 7.39 (t, J=7.2, 1H), 4.04 (q, J=1.0, 1H), 2.16 (m, 1H), 2.13 (q, J=7.6, 2H), 1.84-1.68 (m, 3H), 1.55-1.36 (m, 3H), 1.22-1.11 (m, 2H), 1.01 (t, J=7.6, 3H), 0.89 (s, 3H), 0.83 (d, J=6.8, 3H), 0.54 (s, 3H). $^{13}$C NMR: δ 140.2 (s), 126.4 (d), 67.0 (t), 51.3 (d), 45.1 (d), 42.3 (s), 30.0 (t), 28.3 (2t), 25.7 (q), 21.0 (t), 14.4 (q), 13.9 (q), 13.2 (q). MS: 210($M^+$, 2), 195(3), 177(5), 123(12), 111(34), 110(29), 109 (35), 95(45), 82(19), 69(100), 67(18), 57(28), 55(49), 43(17), 41(36).

c) 1-Ethyl-2-[[(1R)-2,2,3-trimethylcyclopentyl]methyl]cyclopropyl]methanol (1a)

Dibromomethane (2 ml) and acetyl bromide (1 drop) were added to a suspension of ground mixture of zinc (6.5 g, 0.10 mol) and cuprous bromide (0.86 g, 6 mmol) in diethyl ether (40 ml). The reaction was started by heating the flask with a heat-gun. After 10 min., a solution of 2-ethyl-4-[(1R)-2,2,3-trimethylcyclopentyl]but-2-en-1-ol (4a; 5.0 g, 24 mmol) in diethyl ether (50 ml) was added, followed by more dibromomethane (total 17.4 g, 0.10 mol; during 6 h) dissolved in the same solvent (30 ml). After additional 18 h stirring at room temperature, the reaction mixture was diluted with MTBE (100 ml) and filtered over Celite®. The filtrate was washed with cold 1N HCl (50 ml) and brine (2×100 ml), dried ($MgSO_4$), concentrated in vacuo and the residue (4.8 g) was purified by flash chromatography (MTBE/hexane 1:5) to afford 1-ethyl-2-[[(1R)-2,2,3-trimethylcyclopentyl]methyl] cyclopropyl]methanol (1a, 2.9 g, 54% yield, colourless liquid; GC/MS: 2 main diastereomeric pairs of enantiomers 49.5+47.5%).

Main diastereoisomer (first eluted (GC)): $^1$H NMR: δ 3.43 (d, $J_{AB}$=11.1, 1H), 3.31 (d, $J_{AB}$=11.1, 1H), 1.96-1.82 (m, 1H), 1.81-1.70 (m, 1H), 1.62-1.29 (m, 5H), 1.28-1.11 (m, 4H), 0.99 (t, J=7.4, 3H), 0.85 (s, 3H), 0.83 (d, J=6.8, 3H), 0.71-0.59 (m, 1H), 0.50 (s, 3H), 0.43 (dd, J=9.0, 4.5, 1H), −0.08 (dd, J=5.7, 4.5, 1 H). $^{13}$C NMR: δ 69.3 (t), 51.3 (d), 45.2 (d), 42.2 (s), 30.1 (t), 29.1 (t), 28.3 (t), 27.9 (s), 25.6 (q), 22.1 (d), 22.0 (t), 15.6 (t), 14.4 (q), 13.9 (q), 11.2 (q). MS: 224($M^+$, <1), 209(2), 191(4), 137(23), 123(25), 111(28), 110(22), 109(55), 96(22), 95(63), 83(26), 81(36), 72(27), 70(100), 69(93), 67(33), 53(14), 55(63), 43(29), 41(58).

Second major diastereoisomer: $^1$H NMR: δ 3.49 (d, $J_{AB}$=11.1, 1H), 3.22 (d, $J_{AB}$=11.1, 1H), 1.96-1.82 (m, 1H), 1.81-1.70 (m, 1H), 1.62-1.29 (m, 5H), 1.28-1.11 (m, 3H), 1.03 (ddd, J=13.3, 11.0, 7.1, 1H), 0.99 (t, J=7.4, 3H), 0.85 (s, 3H), 0.83 (d, J=6.8, 3H), 0.71-0.59 (m, 1H), 0.49 (s, 3H), 0.48 (dd, J=9.0, 4.5, 1H), 0.00 (dd, J=5.8, 4.5, 1H). $^{13}$C NMR: δ 69.4 (t), 51.8 (d), 45.0 (d), 42.4 (s), 30.2 (t), 29.6 (t), 28.4 (t), 27.0 (s), 25.6 (q), 22.3 (d), 21.4 (t), 16.1 (t), 14.3 (q), 13.9 (q), 11.3 (q). MS: 224($M^+$, 1), 209(3), 191(4), 137(23), 123(26), 111(28), 110(22), 109(53), 96(24), 95(61), 83(27), 81(35), 72(27), 70(100), 69(93), 67(33), 53(14), 55(62), 43(28), 41(57).

Odour description: sandalwood, natural, dry.

EXAMPLE 2

[1-Methyl-2-[[(1R)-2,2,3-trimethylcyclopentyl]methyl]cyclopropyl]methanol (1b); e. e.=80%

Prepared starting from known 2-methyl-4-(2,2,3-trimethylcyclopentyl)but-2-en-1-ol (4b) according to the experimental procedure described in Example 1c as colourless liquid; GC/MS: 2 main diastereomeric pairs of enantiomers 47+50%.

$^1$H NMR: δ 3.35 (d, $J_{AB}$=10.9, 1H), 3.34 (d, $J_{AB}$=9.9, 1H), 3.32 (d, $J_{AB}$=9.9, 1H), 3.30 (d, $J_{AB}$=10.9, 1H), 1.96-1.69 (m, 6H), 1.57-1.37(m, 5H), 1.29-1.05 (m, 7H), 1.14 (s, 3H), 1.13 (s, 3H), 0.86 (2s, 6H), 0.83 (2d, J=6.8, 6H), 0.67 (m, 2H), 0.55 (m, 2H), 0.50 (s, 3H), 0.49 (s, 3H), 0.00 (dd, J=5.3, 4.5, 1H), -0.08 (dd, J=5.6, 4.2, 1H). $^{13}$C NMR: δ 72.7 (t), 72.6 (t), 51.8 (d), 51.3 (d), 45.1 (d), 45.0 (d), 42.4 (s), 42.1 (s), 30.2 (t), 30.1 (t), 30.0 (t), 29.3 (t), 28.3 (2t), 25.7 (q), 25.6 (q), 22.7 (s), 21.8 (s), 21.4 (d), 21.1 (d), 17.1 (t), 16.5 (t), 15.7 (q), 15.1 (q), 14.4 (q), 14.3 (q), 13.9 (2q). MS: main diastereoisomer (second eluted (GC)): 210(M$^+$, 1), 195(4), 177(4), 153(18), 137(30), 123(26), 111(32), 110(23), 109(56), 96(24), 95(58), 83(28), 82(25), 81(40), 69(100), 67(30), 58(33), 57(32), 55(58), 43(33), 41(57); second major diastereoisomer: 210(M$^+$, 1), 195(5), 177(5), 153(17), 137(29), 123(25), 111(32), 110(24), 109(58), 96(23), 95(59), 83(28), 82(23), 81(41), 69(100), 67(30), 58(33), 57(31), 55(59), 43(34), 41(58).

Odour description: sandalwood, creamy, very natural, reminiscence of Atlas cedarwood.

EXAMPLE 3

1-[1-Methyl-2-[[(1S)-2,2,3-trimethylcyclopentyl] methyl]cyclopropyl]ethanol (1c); e. e.=25%

Prepared starting from known 3-methyl-5-(2,2,3-trimethylcyclopentyl)pent-3-en-2-ol (4c) according to the experimental procedure described in Example 1c as colourless liquid; GC/MS: 4 main diastereomeric pairs of enantiomers (19.5+21+20.5+25.5%) separated by flash chromatography (MTBE/hexane 1:5) into 2×2 pair fractions.

2 first eluted (FC) pairs of enantiomers: $^1$H NMR: δ 3.04 (q, J=6.4, 1H), 3.03 (q, J=6.4, 1H), 1.96-1.84 (m, 2H), 1.82-1.70 (m, 2H), 1.57-1.35 (m, 7H), 1.28-1.06 (m, 7H), 1.19 (d, J=6.4, 3H), 1.19 (d, J=6.4, 3H), 1.03 (s, 3H), 1.02 (s, 3H), 0.86 (s, 3H), 0.86 (s, 3H), 0.83 (2d, J=6.8, 3H), 0.67-0.57 (m, 2H), 0.50 (s, 3H), 0.49 (s, 3H), 0.48-0.42 (m, 2H), −0.03 (dd, J=5.4, 4.6, 1H), −0.11 (dd, J=5.5, 4.6, 1H). $^{13}$C NMR: δ 76.4 (d), 76.1 (d), 51.9 (d), 51.4 (d), 45.2 (d), 45.0 (d), 42.4 (s), 42.2 (s), 30.2 (t), 30.1 (t), 30.0 (t), 29.5 (t), 28.4 (t), 28.3 (t), 25.7 (q), 25.7 (s), 25.6 (q), 24.8 (s), 23.0 (d), 22.5 (d), 19.1 (q), 19.1 (q), 17.0 (t), 16.5 (t), 14.4 (q), 14.3 (q), 13.9 (q), 13.9 (q), 12.1 (q), 11.6 (q). MS: 224(M$^+$, <1), 206(1), 191(5), 165(5), 137 (12), 123(16), 111(23), 110(20), 109(43), 96(20), 95(52), 85(22), 82(22), 81(31), 72(63), 70(100), 69(78), 57(24), 55(48), 43(52), 41(48).

2 last eluted (FC) pairs of enantiomers: $^1$H NMR: δ 2.97 (q, J=6.3, 1H), 2.96 (q, J=6.3, 1H), 1.95-1.82 (m, 2H), 1.80-1.70 (m, 2H), 1.57-1.29 (m, 7H), 1.28-1.09 (m, 7H), 1.19 (d, J=6.3, 3H), 1.19 (d, J=6.3, 3H), 1.04 (s, 3H), 1.03 (s, 3H), 0.86 (s, 3H), 0.85 (s, 3H), 0.83 (2d, J=6.8, 6H), 0.55-0.50 (m, 4H), 0.50 (s, 3H), 0.48 (s, 3H), −0.01 (m, 1H), −0.07 (m, 1H). $^{13}$C NMR: δ 76.5 (d), 76.4 (d), 51.7 (d), 51.3 (d), 45.2 (d), 45.0 (d), 42.4 (s), 42.2 (s), 30.2 (t), 30.1 (t), 29.7 (t), 29.0 (t), 28.4 (t), 28.2 (t), 25.9 (s), 25.7 (q), 25.6 (q), 25.0 (s), 21.2 (d), 20.6 (d), 19.3 (q), 19.2 (q), 18.8 (t), 18.3 (t), 14.4 (q), 14.2 (q), 13.9 (q), 13.9 (q), 12.1 (q), 11.4 (q). 224(M$^+$, <1), 206(1), 191(4), 165(3), 137(12), 123(13), 111(19), 110 (16), 109(36), 96(17), 95(45), 85(18), 82(19), 81(27), 72(48), 70(100), 69(67), 57(20), 55(43), 43(45), 41(42).

Odour description: sandalwood, woody, balsamic.

EXAMPLE 4

Floral-Woody Composition for a Feminine Fine Fragrance

| Ingredient | parts by weight |
|---|---|
| Cepionate ® (methyl 2-(3-oxo-2-pentylcyclopentyl)acetate) | 150 |
| Cosmone ™ ((Z)-3-methylcyclotetradec-5-enone) | 20 |
| Cyclohexal (4-(4-hydroxy-4-methylpentyl)cyclohex-3-enecarbaldehyde) | 75 |
| Dipropylene glycol | 19 |
| Ethylene brassylate | 90 |
| Florol ® (2-isobutyl-4-methyltetrahydro-2H-pyran-4-ol) | 55 |
| Linalyl acetate | 45 |
| Myraldene ™ (4-(4-methylpent-3-enyl)cyclohex-3-enecarbaldehyde) | 8 |
| Nirvanolide ™ ((Z)-13-methyloxacyclopentadec-10-en-2-one) | 100 |
| Peach pure | 1 |
| Pepperwood ™ (3,7-dimethylocta-1,6-dien-3-yl dimethylcarbamate) | 20 |
| Phenylethyl alcohol | 20 |
| Radjanol (2-ethyl-4-(2,2,3-trimethylcyclopent-3-enyl)but-2-en-1-ol) | 25 |
| Rose Bulgary oil | 2 |
| Sandela ® (3-(5,5,6-trimethylbicyclo[2.2.1]hept-2-yl)-cyclohexan-1-ol & isomers) | 200 |
| Thibetolide (oxacyclohexadecan-2-one) | 40 |
| | 870 |

An addition of 100 parts of [1-methyl-2-[[(1R)-2,2,3-trimethylcyclopentyl]methyl]-cyclopropyl]methanol (1b) to this accord makes it more natural and rounder. It enhances the freshness of the floral rosy accord and helps to develop comfort and sensuality of the fragrance.

The invention claimed is:
1. A compound of formula 1

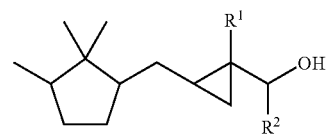

wherein
R$^1$ is methyl or ethyl; and
R$^2$ is hydrogen, methyl or ethyl.
2. A compound according to claim 1 selected from the group consisting of:
[1-ethyl-2-[(2,2,3-trimethylcyclopentyl)methyl]cyclopropyl]methanol,
[1-methyl-2-[(2,2,3-trimethylcyclopentyl)methyl]cyclopropyl]methanol and 1-[1-methyl-2-[(2,2,3-trimethylcyclopentyl)methyl]cyclopropyl]ethanol.

3. A fragrance composition comprising a compound according to claim 1.

4. A fragrance application comprising
a compound of formula 1 according to claim 1 and
a consumer product base.

5. A fragrance application according to claim 4 wherein the consumer product base is selected from the group consisting of: fine fragrance, household product, laundry product, body care product and cosmetic.

6. A method of manufacturing a fragrance composition, comprising the step of: incorporating of an effective amount of a compound of formula 1 according to claim 1 in a base material.

7. A method of improving, enhancing or modifying a fragrance of a fragrance composition or fragrance application comprising the step of incorporating an effective amount of a compound of formula 1 according to claim 1 in a base material.

8. A fragrance composition comprising a compound according to claim 2.

9. A fragrance application comprising
a compound according to claim 2; and
a consumer product base.

10. A fragrance application according to claim 9 wherein the consumer product base is selected from the group consisting of: fine fragrance, household product, laundry product, body care product and cosmetic.

11. A method of manufacturing a fragrance composition, comprising the step of:
incorporating of an effective amount of a compound according to claim 2 in a base material.

12. A method of improving, enhancing or modifying a fragrance of a fragrance composition or fragrance application comprising the step of incorporating an effective amount of a compound according to claim 2 in a base material.

\* \* \* \* \*